US009320656B2

(12) United States Patent
Wang et al.

(10) Patent No.: US 9,320,656 B2
(45) Date of Patent: *Apr. 26, 2016

(54) WATER-DISPERSIBLE THERMOPLASTIC INJECTION MOLDED COMPOSITION

(71) Applicant: Kimberly-Clark Worldwide, Inc., Neenah, WI (US)

(72) Inventors: James H. Wang, Appleton, WI (US); Gregory J. Wideman, Menasha, WI (US); Mark M. Mleziva, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 197 days.

This patent is subject to a terminal disclaimer.

(21) Appl. No.: 14/092,013

(22) Filed: Nov. 27, 2013

(65) Prior Publication Data

US 2015/0148461 A1 May 28, 2015

(51) Int. Cl.
| | | |
|---|---|---|
| *A61F 13/26* | (2006.01) |
| *B29C 45/00* | (2006.01) |
| *C08L 1/28* | (2006.01) |
| *C08L 29/04* | (2006.01) |
| *C08L 1/08* | (2006.01) |
| *C08K 3/22* | (2006.01) |
| *B29L 23/00* | (2006.01) |
| *B29C 45/16* | (2006.01) |

(52) U.S. Cl.
CPC . *A61F 13/26* (2013.01); *C08L 1/28* (2013.01); *C08L 1/284* (2013.01); *C08L 29/04* (2013.01); *B29C 45/0001* (2013.01); *B29C 45/16* (2013.01); *B29K 2995/0062* (2013.01); *B29L 2023/00* (2013.01); *C08K 2003/2241* (2013.01)

(58) Field of Classification Search
CPC ........ A61F 13/26; C08L 1/28; B29C 45/0001
USPC .......................................................... 524/43
See application file for complete search history.

(56) References Cited

U.S. PATENT DOCUMENTS

| | | | |
|---|---|---|---|
| 3,724,462 A | 4/1973 | Hanke |
| 3,882,869 A | 5/1975 | Hanke |
| 4,372,311 A | 2/1983 | Potts |
| 4,499,154 A | 2/1985 | James et al. |
| 4,731,122 A * | 3/1988 | Cortese et al. ........... 106/170.36 |
| 4,900,299 A | 2/1990 | Webb |
| 4,921,474 A | 5/1990 | Suzuki et al. |
| 5,002,526 A | 3/1991 | Herring |
| 5,102,465 A | 4/1992 | Lamond |
| 5,350,354 A | 9/1994 | Billmers |
| 5,367,003 A | 11/1994 | Petcavich |
| 5,378,751 A | 1/1995 | Deibig et al. |
| 5,389,068 A | 2/1995 | Keck |
| 5,393,528 A | 2/1995 | Staab |
| 5,496,874 A | 3/1996 | Faass et al. |
| 5,509,913 A | 4/1996 | Yeo |
| 5,533,990 A | 7/1996 | Yeo |
| 5,695,868 A | 12/1997 | McCormack |
| 5,738,646 A | 4/1998 | Fox et al. |
| 5,804,653 A | 9/1998 | Weng |
| 5,855,999 A | 1/1999 | McCormack |
| 5,868,824 A | 2/1999 | Andersen et al. |
| 5,902,262 A | 5/1999 | Bastioli et al. |
| 5,910,520 A | 6/1999 | Dabi et al. |
| 5,932,497 A | 8/1999 | Morman et al. |
| 5,954,683 A | 9/1999 | Downs et al. |
| 5,997,981 A | 12/1999 | McCormack et al. |
| 6,015,764 A | 1/2000 | McCormack et al. |
| 6,111,163 A | 8/2000 | McCormack et al. |
| 6,123,996 A | 9/2000 | Larsson et al. |
| 6,203,515 B1 | 3/2001 | Norquest |
| 6,248,880 B1 | 6/2001 | Karlson |
| 6,461,457 B1 | 10/2002 | Taylor et al. |
| 6,639,066 B2 | 10/2003 | Boström et al. |
| 6,689,036 B2 | 2/2004 | Balzar et al. |
| 6,706,942 B1 | 3/2004 | Zhao et al. |
| 6,730,057 B2 | 5/2004 | Zhao et al. |
| 6,787,156 B1 | 9/2004 | Bar-Shalom |
| 7,713,253 B2 | 5/2010 | Osborn, III et al. |
| 8,317,765 B2 | 11/2012 | Loyd et al. |
| 8,458,882 B2 | 6/2013 | Mastalish et al. |
| 8,569,402 B2 | 10/2013 | Henderson et al. |
| 2002/0042599 A1 | 4/2002 | Zhao et al. |
| 2003/0040695 A1 | 2/2003 | Zhao et al. |
| 2003/0135180 A1 | 7/2003 | Nguyen et al. |
| 2003/0232911 A1 | 12/2003 | Hwang et al. |

(Continued)

FOREIGN PATENT DOCUMENTS

| | | | |
|---|---|---|---|
| EP | 0 613 672 A1 | 9/1994 |
| EP | 0 635 545 A2 | 1/1995 |
| EP | 0 635 545 A3 | 1/1995 |
| WO | WO 96/04338 A1 | 2/1996 |
| WO | WO 00/15165 A1 | 3/2000 |
| WO | WO 02/085983 A1 | 10/2002 |
| WO | WO 2012/092671 A1 | 7/2012 |
| WO | WO 2013/011301 A1 * | 1/2013 |

OTHER PUBLICATIONS

Kuraray POVAL & EXCEVAL Technical Data Sheet, 8 pages (Undated).*
Klucel (TM), Hydropropylcellulose Technical Data Sheet, 2 pages (Undated).*
International Search Report and Written Opinion for PCT/IB2014/064931 dated Jan. 26, 2015, 13 pages.
Related U.S. Patent Application Form (Dated Jan. 6, 2014).

*Primary Examiner* — Fred M Teskin
(74) *Attorney, Agent, or Firm* — Dority & Manning, P.A.

(57) ABSTRACT

A thermoplastic composition that is water-sensitive (e.g., water-soluble, water-dispersible, etc.) in that it loses its integrity over time in the presence of water that can also be injection molded is provided. The composition contains a cellulose derivative, a synthetic water-soluble polymer, and a plasticizer. The desired water-sensitive and moldable attributes of the composition may be achieved in the present invention by selectively controlling a variety of aspects of the composition, such as the nature of the components employed, the relative amount of each component, the manner in which the composition is formed, and so forth.

28 Claims, 3 Drawing Sheets

(56) References Cited

U.S. PATENT DOCUMENTS

| | | |
|---|---|---|
| 2006/0016714 A1 | 1/2006 | Fregonese et al. |
| 2006/0025541 A1 | 2/2006 | Bourgoin et al. |
| 2007/0232982 A1 | 10/2007 | Jarmon et al. |
| 2010/0016780 A1 | 1/2010 | VanDenBogart et al. |
| 2010/0055231 A1* | 3/2010 | Song et al. ................ 426/3 |
| 2010/0297458 A1 | 11/2010 | Khemani et al. |
| 2011/0250241 A1 | 10/2011 | Duffield et al. |
| 2012/0328804 A1 | 12/2012 | Allen et al. |
| 2013/0281912 A1 | 10/2013 | Mikhail |
| 2015/0148732 A1* | 5/2015 | Wang et al. ................ 604/11 |

* cited by examiner of the invention

WATER-DISPERSIBLE THERMOPLASTIC INJECTION MOLDED COMPOSITION

BACKGROUND OF THE INVENTION

Flushable feminine care products provide consumers with discretion and convenience benefits. However, current plastic tampon applicators are made of injection molded materials such as polyolefins (e.g., polypropylenes or polyethylenes) and polyesters that are not biodegradable or renewable as the use of biodegradable polymers in an injection molded part is problematic due to the difficulty involved with thermally processing such polymers and high cost. As such, consumers must dispose of tampon applicators in a separate waste receptacle, which results in a challenge for consumers to dispose of the applicators in a discrete and convenient manner. Furthermore, the soiled or used tampon applicator may also pose a biohazard or potential health hazard. As a result, although current plastic tampon applicators are not supposed to be flushed down the toilet, some consumers may nevertheless attempt to flush the applicators in the toilet, which can lead to clogging of sewer pipes and municipal waste water treatment facilities. Attempts have been made to injection mold water-dispersible materials such as cellulose derivatives or polyvinyl alcohol in order to alleviate these problems, but such attempts have not been successful. Instead, when using either cellulose derivatives or polyvinyl alcohol in tampon applicators, the materials must be solution processed so that they can be formed into a tampon applicator that has a thick enough wall, and such solution processing is a slow, costly, environmentally unsustainable process that necessitates high energy requirements. Further, although cardboard applicators have been developed, the cardboard must often be coated to decrease the coefficient of friction of the applicator to a comfortable level for consumers, and such coatings are not environmentally friendly and add to the costs associated with forming the applicator.

As such, a need currently exists for a water-dispersible composition that can also be injection molded, where such composition can be successfully formed into a tampon applicator. A need also exists for a water-dispersible applicator that is comfortable to insert and that does not being to break down upon insertion.

SUMMARY OF THE INVENTION

In accordance with one embodiment of the present invention, a water-dispersible composition is disclosed that comprises from about 7 wt. % to about 70 wt. % of at least one cellulose derivative; from about 7 wt. % to about 70 wt. % of at least one synthetic water-soluble polymer; and from about 2 wt. % to about 50 wt. % of at least one plasticizer based on the total weight of the composition, wherein the weight percentage ratio of the synthetic water-soluble polymer to the cellulose derivative ranges from about 0.1 to about 10, further wherein the composition is thermoplastic.

In one embodiment, the cellulose derivative can constitute from about 20 wt. % to about 60 wt. % of the composition based on the total weight of the composition. In yet another embodiment, the synthetic water-soluble polymer can constitutes from about 20 wt. % to about 60 wt. % of the composition based on the total weight of the composition. In still another embodiment, the plasticizer can constitute from about 5 wt. % to about 40 wt. % of the composition based on the total weight of the composition. In an additional embodiment, the weight percentage ratio of the synthetic water-soluble polymer to the cellulose derivative ranges from about 0.3 to about 3.0.

In still another embodiment, the cellulose derivative can be a nonionic cellulosic ether, and, in some embodiments, the nonionic cellulosic ether can be a hydroxypropyl methylcellulose. In some instances, the hydroxypropyl methylcellulose can have a methoxyl content of from about 10% to about 40%. Further, in some instances, the hydroxypropyl methylcellulose can have a hydroxypropyl content of from about 1% to about 15%. In addition, in some embodiments, the nonionic cellulosic ether can have a viscosity ranging from about 1,000 mPa·s to about 75,000 mPa·s for a 2% aqueous solution at 20° C.

In another embodiment, the synthetic water-soluble polymer can be a vinyl alcohol polymer, such as a vinyl alcohol polymer that is partially hydrolyzed. The vinyl alcohol polymer can have a degree of hydrolysis of from about 80 mole % to about 90 mole %.

In yet another embodiment, the plasticizer can be a polyhydric alcohol. For instance, the plasticizer can be a polyol, such as ethylene glycol, glycerol, propylene glycol, dipropylene glycol, butylene glycol, hexane triol, or a combination thereof.

In another embodiment, the composition can further include from about 0.5 wt. % to about 35 wt. % of an inorganic particulate filler based on the total weight of the composition. The inorganic particulate filler can be calcium carbonate, kaolin clay, silica, alumina, barium carbonate, sodium carbonate, titanium dioxide, zeolites, magnesium carbonate, calcium oxide, magnesium oxide, aluminum hydroxide, talc, or a combination thereof.

In one particular embodiment, the composition can exhibit a melt flow index of from about 10 grams per 10 minutes to about 150 grams per 10 minutes when subjected to a load of 2160 grams at a temperature of 190° C. according to ASTM Test Method D1238-E.

In still another embodiment, the water-dispersible thermoplastic composition can be formed into a molded article. In some embodiments, the molded article can disintegrate in tap water in less than about 18 hours. Further, in some embodiments, the molded article can be a tampon applicator.

In accordance with another embodiment of the present invention, a method for forming an injection molded part is described. The method includes injecting a water-dispersible, thermoplastic composition into a mold cavity, wherein the thermoplastic composition comprises from about 7 wt. % to about 70 wt. % of a cellulose derivative, from about 7 wt. % to about 70 wt. % of a synthetic water-soluble polymer, and from about 2 wt. % to about 50 wt. % of a plasticizer; and shaping the thermoplastic composition into a molded part within the mold cavity.

In another embodiment, the method can also include coating the injection molded part with a water-insoluble coating. In another embodiment, the method can include a co-injection molding process, wherein the injection molded part is a two layered molded part having an inner layer and an outer layer, wherein the inner layer comprises the injection-molded, thermoplastic composition and the outer layer is water-insoluble. Further, the outer layer can include from about 1 wt. % to about 50 wt. % of the injection molded part and the inner layer can include from about 50 wt. % to about 99 wt. % of the injection molded part. In addition, the water-insoluble layer comprises a wax, silicon, polytetrafluoroethylene, polyethylene, a polyester, polyamide, a thermoplastic elastomer (e.g., polyurethane or a polyolefin-based elastomer), or a combination thereof.

In yet another embodiment, the cellulose derivative can be a hydroxypropyl methylcellulose. In an additional embodiment, the synthetic water-soluble polymer can be a polyvinyl alcohol. Further, the molded part can be in the form of a tampon applicator.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
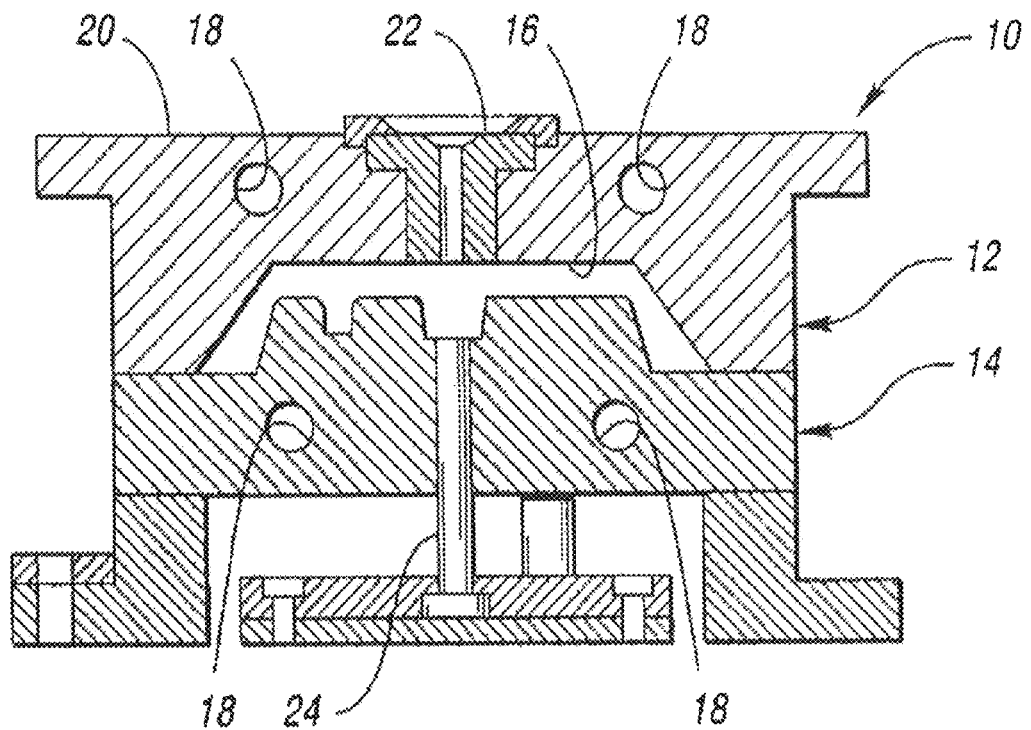
FIG. 1 is a schematic illustration of one embodiment of an injection molding apparatus for use in the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a composition that is water-sensitive (e.g., water-soluble, water-dispersible, etc.) in that it loses its integrity over time in the presence of water, yet is also thermoplastic with a high enough melt flow index and a low enough melt viscosity such that it can be injection molded. The composition contains a natural cellulose derivative, a synthetic water-soluble polymer, and a plasticizer. The desired water-sensitive attributes of the composition may be achieved in the present invention by selectively controlling a variety of aspects of the composition, such as the nature of the components employed, the relative amount of each component, the ratio of the weight percentage of one component to the weight percentage of another component, the manner in which the composition is formed, and so forth. In this regard, various embodiments of the present invention will now be described in more detail below.

I. Composition Components

A. Cellulose Derivative

The water-dispersible, thermoplastic composition includes a cellulose derivative (e.g., cellulosic ethers or esters). In one particular embodiment, for instance, the cellulose derivative is a nonionic, cationic, anionic, and/or amphoteric cellulosic ether. Nonionic cellulose ethers, for instance, may be produced in any manner known to those skilled in the art, such as by reacting alkali cellulose with ethylene oxide and/or propylene oxide, followed by reaction with methyl chloride, ethyl chloride and/or propyl chloride. Nonionic cellulosic ethers and methods for producing such ethers are described, for instance, in U.S. Pat. No. 6,123,996 to Larsson, et al.; U.S. Pat. No. 6,248,880 to Karlson; and U.S. Pat. No. 6,639,066 to Bostrom, et al., which are incorporated herein in their entirety by reference thereto for all purposes. Some suitable examples of nonionic cellulosic ethers include, but are not limited to, water-soluble alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, hydroxypropyl methylcellulose, ethyl hydroxyethyl cellulose, ethyl hydroxypropyl cellulose, methyl ethyl hydroxyethyl cellulose and methyl ethyl hydroxypropyl cellulose; and so forth. Preferred nonionic cellulosic ethers for use in the composition of the present invention are ethyl hydroxyethyl cellulose, methylethyl hydroxyethyl cellulose, methylethyl hydroxyethyl hydroxypropyl cellulose, and hydroxypropyl methylcellulose.

Particularly suitable cellulosic ethers may include, for instance, those available from Dow Chemical under the name METHOCEL™ and having a methoxyl content of from about 10% to about 40%, such as from about 15% to about 30% and a hydroxypropyl content of from about 1% to about 15%, such as from about 2% to about 10%. Such hydroxypropyl methylcellulose cellulose derivatives can have a viscosity determined 2% in an aqueous solution at 20° C. ranging from about 1,000 mPa·s to about 75,000 mPa·s, such as from about 2,000 mPa·s to about 50,000 mPa·s, such as from about 3,000 mPa·s to about 25,000 mPa·s, such as from about 4,000 mPa·s to about 15,000 mPa·s. One suitable cellulosic ether is METHOCEL™ 40-100, a hydroxypropyl methylcellulose having a methoxyl content of 18%, a hydroxypropyl content of 5%, and a viscosity of 12,000 mPa·s. Another suitable cellulosic ether is METHOCEL™ 40-202, a hydroxypropyl methylcellulose having a methoxyl content of 29%, a hydroxypropyl content of 8.5%, and a viscosity of 4,000 mPa·s.

Other suitable cellulosic ethers are those available from Akzo Nobel of Stamford, Conn. under the name BERMOCOLL™. Still other suitable cellulosic ethers are those available from Shin-Etsu Chemical Co., Ltd. of Tokyo, Japan under the name METOLOSE™, including METOLOSE™ Type SM (methylcellulose), METOLOSE™ Type SH (hydroxypropyl methyl cellulose), and METOLOSE™ Type SE (hydroxyethylmethyl cellulose). Other suitable cellulosic ethers are also available from Hercules, Inc. of Wilmington, Del. under the name CULMINAL™. Further examples of suitable polysaccharides are described in more detail above.

The cellulose derivative can be present in the water-dispersible, thermoplastic composition in an amount ranging from about 7 wt. % to about 70 wt. %, such as from about 15 wt. % to about 65 wt. %, such as from about 20 wt. % to about 60 wt. %, such as from about 25 wt. % to about 50 wt. % based on the total weight of the composition.

B. Synthetic Water-Soluble Polymer

The water-dispersible, thermoplastic composition also includes one or more synthetic water-soluble polymers. Such polymers may be formed from monomers such as vinyl pyrrolidone, hydroxyethyl acrylate or methacrylate (e.g., 2-hydroxyethyl methacrylate), hydroxypropyl acrylate or methacrylate, acrylic or methacrylic acid, acrylic or methacrylic esters or vinyl pyridine, acrylamide, vinyl acetate, vinyl alcohol, ethylene oxide, derivatives thereof, and so forth. Other examples of suitable monomers are described in U.S. Pat. No. 4,499,154 to James, et al., which is incorporated herein in its entirety by reference thereto for all purposes. The resulting polymers may be homopolymers or interpolymers (e.g., copolymer, terpolymer, etc.), and may be nonionic, anionic, cationic, or amphoteric. In addition, the polymer may be of one type (i.e., homogeneous), or mixtures of different polymers may be used (i.e., heterogeneous).

In one particular embodiment, the water-soluble polymer contains a repeating unit having a functional hydroxyl group, such as polyvinyl alcohol ("PVOH"), copolymers of polyvinyl alcohol (e.g., ethylene vinyl alcohol copolymers, methyl methacrylate vinyl alcohol copolymers, etc.), etc. Vinyl alcohol polymers, for instance, have at least two or more vinyl alcohol units in the molecule and may be a homopolymer of vinyl alcohol, or a copolymer containing other monomer units. Vinyl alcohol homopolymers may be obtained by hydrolysis of a vinyl ester polymer, such as vinyl formate, vinyl acetate, vinyl propionate, etc. Vinyl alcohol copolymers may be obtained by hydrolysis of a copolymer of a vinyl ester with an olefin having 2 to 30 carbon atoms, such as ethylene, propylene, 1-butene, etc.; an unsaturated carboxylic acid having 3 to 30 carbon atoms, such as acrylic acid, methacrylic acid, crotonic acid, maleic acid, fumaric acid, etc., or an ester, salt, anhydride or amide thereof; an unsaturated nitrile having 3 to 30 carbon atoms, such as acrylonitrile, methacrylonitrile, etc.; a vinyl ether having 3 to 30 carbon atoms, such as methyl vinyl ether, ethyl vinyl ether, etc.; and so forth. The degree of hydrolysis may be selected to optimize solubility, etc., of the polymer. For example, the degree of hydrolysis may be from about 60 mole % to about 95 mole %, in some embodiments from about 80 mole % to about 90 mole %, in some embodiments, from about 85 mole % to about 89 mole %, and in some embodiments, from about 87 mole % to about 89 mole %. Examples of suitable partially hydrolyzed polyvinyl alcohol polymers are available under the designation CELVOL™ 203, 205, 502, 504, 508, 513, 518, 523, 530, or 540 from Celanese Corp. Other suitable partially hydrolyzed polyvinyl alcohol polymers are available under the designation ELVANOL™ 50-14, 50-26, 50-42, 51-03, 51-04, 51-05, 51-08, and 52-22 from DuPont.

The synthetic water-soluble polymer can be present in the water-dispersible, thermoplastic composition in an amount ranging from about 7 wt. % to about 70 wt. %, such as from about 15 wt. % to about 65 wt. %, such as from about 20 wt. % to about 60 wt. %, such as from about 25 wt. % to about 55 wt. %, such as from about 30 wt. % to about 50 wt. % based on the total weight of the composition. Further, the ratio of the synthetic water-soluble polymer present in the composition to the cellulose derivative present in the composition can range from about 0.1 to about 10, such as from about 0.3 to about 3, such as from about 0.6 to about 1.7, such as from about 0.65 to about 1.6.

C. Plasticizer

A plasticizer is also employed in the water-dispersible, thermoplastic composition to help render the cellulose derivative and the water-soluble polymer thermoplastic and thus suitable for extrusion into pellets and subsequent injection molding. Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), polyethylene glycols, etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as ethylene acrylic acid, ethylene maleic acid, butadiene acrylic acid, butadiene maleic acid, propylene acrylic acid, propylene maleic acid, and other hydrocarbon based acids. A low molecular weight plasticizer is preferred, such as less than about 20,000 g/mol, preferably less than about 5,000 g/mol and more preferably less than about 1,000 g/mol.

The plasticizer may be incorporated into the composition of the present invention using any of a variety of known techniques. For example, the cellulose derivative and/or water-soluble polymers may be "pre-plasticized" prior to incorporation into the composition. Alternatively, one or more of the components may be plasticized at the same time as they are blended together. Regardless, batch and/or continuous melt blending techniques may be employed to blend the components. For example, a mixer/kneader, Banbury mixer, Farrel continuous mixer, single-screw extruder, twin-screw extruder, roll mill, etc., may be utilized. One particularly suitable melt-blending device is a co-rotating, twin-screw extruder (e.g., USALAB twin-screw extruder available from Thermo Electron Corporation of Stone, England or an extruder available from Werner-Pfleiderer from Ramsey, N.J.). Such extruders may include feeding and venting ports and provide high intensity distributive and dispersive mixing. For example, the cellulose derivative and water-soluble polymer may be initially fed to a feeding port of the twin-screw extruder to form a composition. Thereafter, a plasticizer may be injected into the composition. Alternatively, the composition may be simultaneously fed to the feed throat of the extruder or separately at a different point along the length of the extruder. Melt blending may occur at any of a variety of temperatures, such as from about 30° C. to about 240° C., in some embodiments, from about 40° C. to about 200° C., and in some embodiments, from about 50° C. to about 150° C.

Plasticizers can be present in the water-dispersible, thermoplastic composition in an amount ranging from about 2 wt. % to about 50 wt. %, such as from about 3 wt. % to about 45 wt. %, such as from about 5 wt. % to about 40 wt. %, such as from about 10 wt. % to about 35 wt. % based on the total weight of the composition. In some embodiments, the amount of plasticizer present should be greater than 15 wt. % so that the polymer composition in which it is utilized can be extruded and flow well from the die for pelletizing and then injection molding. For instance, the amount of plasticizer can be present in the water-dispersible, thermoplastic composition in an amount ranging from about 25 wt. % to about 50 wt. %.

D. Fillers

Although the combination of the cellulose derivative, water-soluble polymer, and plasticizer may achieve the desired water-solubility required for a water-dispersible, injection molded composition, it is still often difficult to achieve a precise set of mechanical properties as desired for injected molded articles. In this regard, the composition can also contain one or more fillers. Due to its rigid nature, the amount of the filler may be readily adjusted to fine tune the composition to the desired degree of ductility (e.g., peak elongation) and stiffness (e.g., modulus of elasticity).

The filler of the present invention may include particles having any desired size, such as those having an average size of from about 0.5 to about 10 micrometers, in some embodiments, from about 1 to about 8 micrometers, and in some embodiments, from about 2 to about 6 micrometers. Suitable particles for use as a filler may include inorganic oxides, such as calcium carbonate, kaolin clay, silica, alumina, barium carbonate, sodium carbonate, titanium dioxide, zeolites, magnesium carbonate, calcium oxide, magnesium oxide, aluminum hydroxide, talc, etc.; sulfates, such as barium sulfate, magnesium sulfate, aluminum sulfate, etc.; cellulose-type powders (e.g., pulp powder, wood powder, etc.); carbon; cyclodextrins; synthetic polymers (e.g., polystyrene), and so forth. Still other suitable particles are described in U.S. Pat. Nos. 6,015,764 and 6,111,163 to McCormack, et al.; U.S. Pat. No. 5,932,497 to Morman, et al.; U.S. Pat. No. 5,695,868 to McCormack; U.S. Pat. No. 5,855,999 to McCormack, et al.; U.S. Pat. No. 5,997,981 to McCormack et al.; and U.S. Pat. No. 6,461,457 to Taylor, et al., which are incorporated herein in their entirety by reference thereto for all purposes.

In one particular embodiment, the filler includes particles formed from calcium carbonate. If desired, calcium carbonate particles may be employed that have a purity of at least about 95 wt. %, in some embodiments at least about 98 wt. %, and in some embodiments, at least about 99 wt. %. Such high purity calcium carbonates are generally fine, soft, and round, and thus provide a more controlled and narrow particle size for improving the properties of the composition. An example of such a high purity calcium carbonate is Caribbean micritic calcium carbonate, which is mined from soft and friable, finely divided, chalk-like marine sedimentary deposits frequently occurring as surface deposits in the Caribbean (e.g., Jamaica). Such calcium carbonates typically have an average particle size of about 10 micrometers or less, and desirably about 6 micrometers or less. Other examples of Caribbean micritic calcium carbonates are described in U.S. Pat. No. 5,102,465 to Lamond, which is incorporated herein in its entirety by reference thereto for all purposes. Such calcium carbonates may be wet or dry ground, and classified into a narrow particle size distribution with round or spherical-shaped particles. One particularly suitable micritic calcium carbonate is available from Specialty Minerals under the designation "MD1517."

Although not required, the filler may optionally be coated with a modifier (e.g., fatty acid, such as stearic acid or behenic acid) to facilitate the free flow of the particles in bulk and their ease of dispersion into the composition. The filler may be pre-compounded with such additives before mixing with the other components of the composition, or the additives may be compounded with the other components of the composition and fillers at the melt-blending step.

When present, the fillers can be present in an amount ranging from about 0.5 wt. % to about 35 wt. %, such as from about 1 wt. % to about 30 wt. %, such as from about 2 wt. % to about 25 wt. %, such as from about 3 wt. % to about 20 wt. % based on the total weight of the water-dispersible, thermoplastic composition.

E. Coloring Agents

In addition, the water-dispersible, thermoplastic composition can contain one or more coloring agents (e.g., pigment or dye). Typically, a pigment refers to a colorant based on inorganic or organic particles which do not dissolve in water or solvents. Usually pigments form an emulsion or a suspension in water. On the other hand, a dye generally refers to a colorant that is soluble in water or solvents.

The pigment or dye can be present in an amount effective to be visible once the composition is formed into an injection molded article so that articles from the composition can have an aesthetically pleasing appearance to the user. Suitable organic pigments, include dairylide yellow AAOT (for example, Pigment Yellow 14 CI No. 21 095), dairylide yellow AAOA (for example, Pigment Yellow 12 CI No. 21090), Hansa Yellow, CI Pigment Yellow 74, Phthalocyanine Blue (for example, Pigment Blue 15), lithol red (for example, Pigment Red 52:1 CI No. 15860:1), toluidine red (for example, Pigment Red 22 CI No. 12315), dioxazine violet (for example, Pigment Violet 23 CI No. 51319), phthalocyanine green (for example, Pigment Green 7 CI No. 74260), phthalocyanine blue (for example, Pigment Blue 15 CI No. 74160), naphthoic acid red (for example, Pigment Red 48:2 CI No. 15865:2). Inorganic pigments include titanium dioxide (for example, Pigment White 6 CI No, 77891), iron oxides (for example, red, yellow, and brown), chromium oxide (for example, green), ferric ammonium ferrocyanide (for example, blue), and the like.

Suitable dyes that may be used include, for instance, acid dyes, and sulfonated dyes including direct dyes. Other suitable dyes include azo dyes (e.g., Solvent Yellow 14, Dispersed Yellow 23, and Metanil Yellow), anthraquinone dyes (e.g., Solvent Red 111, Dispersed Violet 1, Solvent Blue 56, and Solvent Orange 3), xanthene dyes (e.g., Solvent Green 4, Acid Red 52, Basic Red 1, and Solvent Orange 63), azine dyes, and the like.

When present, the coloring agents can be present in the water-dispersible, thermoplastic composition in an amount ranging from about 0.5 wt. % to about 20 wt. %, such as from about 1 wt. % to about 15 wt. %, such as from about 1.5 wt. % to about 12.5 wt. %, such as from about 2 wt. % to about 10 wt. % based on the total weight of the water-dispersible, thermoplastic composition.

F. Other Optional Components

In addition to the components noted above, other additives may also be incorporated into the composition of the present invention, such as dispersion aids, melt stabilizers, processing stabilizers, heat stabilizers, light stabilizers, antioxidants, heat aging stabilizers, whitening agents, antiblocking agents, bonding agents, lubricants, etc. Dispersion aids, for instance, may also be employed to help create a uniform dispersion of the cellulose derivative/polyvinyl alcohol/plasticizer mixture and retard or prevent separation into constituent phases. Likewise, the dispersion aids may also improve the water dispersibility of the composition. Although any dispersion aid may generally be employed in the present invention, surfactants having a certain hydrophilic/lipophilic balance ("HLB") may improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some embodiments of the present invention, the HLB value of the surfactants is from about 1 to about 20, in some embodiments from about 1 to about 15 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

When employed, the dispersion aids) typically constitute from about 0.01 wt. % to about 15 wt. %, such as from about 0.1 wt. % to about 10 wt. %, such as from about 0.5 wt. % to about 5 wt. %, such as from about 1 wt. % to about 3 wt. % based on the total weight of the water-dispersible, thermoplastic composition.

II. Molded Parts

A molded part can be formed from the composition of the present disclosure using any of a variety of techniques known in the art, such as extrusion blow molding, injection molding, rotational molding, compression molding, etc., as well as combinations of the foregoing. For instance, the present inventors have found that through the selective control of the specific components of the composition and their weight percentage ratios, a thermoplastic composition having a high enough melt flow index and a low enough viscosity for use injection molding applications can be achieved. The melt flow index of the water-dispersible, thermoplastic composition may also range from about 10 grams per 10 minutes to about 150 grams per 10 minutes, in some embodiments from about 15 grams per 10 minutes to about 125 grams per 10 minutes, and in some embodiments, from about 20 grams per 10 minutes to about 100 grams per 10 minutes. The melt flow index is the weight of a polymer (in grams) that may be forced through an extrusion rheometer orifice (0.0825-inch diameter) when subjected to a load of 2160 grams in 10 minutes at a certain temperature (e.g., 190° C.), measured in accordance with ASTM Test Method D1238-E. Meanwhile, the viscosity is a low enough viscosity so that the composition of the present invention can be extruded and also pushed through an orifice into a mold during injection molding, for example.

Regardless of the molding process selected, the thermoplastic composition may be used alone to form the molded part, or in combination with other polymeric components to form a molded part. For example, other polymer(s) can be injected or transferred into a mold during a co-injection molding process to form a water-insoluble skin layer around a water-dispersible core layer of the composition of the present invention. Tie layers between the core layer and skin layer may also be formed. Examples of machines suitable for co-injection, sandwich, or two-component molding include machines produced by Presma Corp., Northeast Mold & Plastics, Inc. Although not required, the core of such a molded part is typically formed from the thermoplastic composition of the present invention and the skin layer is typically formed from a different material (e.g., a wax, a silicon (e.g., polysiloxane), polytetrafluoroethylene, a polyolefin (e.g., polyethylene), a polyester, a polyamide, a thermoplastic elastomer (e.g., polyurethane or a polyolefin-based elastomer), or a combination thereof), that enhances the surface properties on the molded part. For instance, when the molded part is a tampon applicator, the skin layer can have a reduced coefficient of friction to provide more comfort to the user. In addition, the skin layer can have a lower level of water sensitivity such that the applicator is less likely to begin disintegrating during use.

Referring to FIG. 1, for example, one particular embodiment of a single-component injection molding apparatus or tool 10 that may be employed in the present invention is shown in more detail. In this embodiment, the apparatus 10 includes a first mold base 12 and a second mold base 14, which together define an article or component-defining mold cavity 16. Each of the mold bases 12 and 14 includes one or more cooling lines 18 through which a cooling liquid such as water flows to cool the apparatus 10 during use. The molding apparatus 10 also includes a resin flow path that extends from an outer exterior surface 20 of the first mold half 12 through a sprue 22 to the mold cavity 16. The resin flow path may also include a runner and a gate, both of which are not shown for purposes of simplicity. The molding apparatus 10 also includes one or more ejector pins 24 slidably secured within the second mold half 14 that helps to define the mold cavity 16 in the closed position of the apparatus 10, as indicated in FIG. 1. The ejector pin 24 operates in a well-known fashion to remove a molded part from the cavity 16 in the open position of the molding apparatus 10.

The thermoplastic composition may be directly injected into the molding apparatus 10 using techniques known in the art. For example, the molding material may be supplied in the form of pellets to a feed hopper attached to a barrel that contains a rotating screw (not shown). As the screw rotates, the pellets are moved forward and undergo extreme pressure and friction, which generates heat to melt the pellets. Electric heater bands (not shown) attached to the outside of the barrel may also assist in the heating and temperature control during the melting process. For example, the bands may be heated to a temperature of from about 200° C. to about 260° C., in some embodiments from about 230° C. to about 255° C., and in some embodiments, from about 240° C. to about 250° C. Upon entering the molding cavity 16, the molding material is solidified by the cooling liquid flowing through the lines 18. The cooling liquid may, for example, be at a temperature (the "molding temperature") of from about 5° C. to about 50° C., in some embodiments from about 10° C. to about 40° C., and in some embodiments, from about 15° C. to about 30° C.

The molded parts may have a variety of different sizes and configurations. For instance, the molded parts may be used to form various parts used in "personal care" applications. For instance, in one particular embodiment, the molded part is used to form a tampon applicator that is water-dispersible. The molded part can disintegrate in tap water in less than about 18 hours, such as less than about 12 hours, such as less than about 4 hours. In some embodiments, the molded part can disintegrate in tap water in less than about 3 hours, such as less than about 2 hours, such as in from about 5 minutes to about 100 minutes.

Molded parts containing the water-dispersible, thermoplastic composition of the present invention can have a degree of expansion in the width direction of about 1% or less, such as from about 0.1% to about 1%, such as from about 0.2% to about 0.9%, such as from about 0.3% to about 0.8% as determined in accordance with ASTM D955-08. Meanwhile, the molded parts of the present invention can have a degree of shrinkage in the length direction of about 0.5% or less, such as from about 0.05% to about 5%, such as from about 0.1% to about 0.4%, such as from about 0.15% to about 0.3%. Because the degree of expansion in the width direction is low, the parts can fit in the same mold for secondary injection if desired.

Further, molded parts containing the water-dispersible, thermoplastic composition of the present invention can have a tensile strength of from about 1 MPa to about 40 MPa, such as from about 2.5 MPa to about 30 MPa, such as from about 5 MPa to about 20 MPa; an elongation at break of from about 2% to about 50%, such as from about 6% to about 40%, such as from about 8% to about 30%; a modulus of from about 50 MPa to about 1100 MPa, such as from about 60 MPa to about 1000 MPa, such as from about 70 MPa to about 900 MPa; and an elongation at yield of from about 2.5% to about 30%, such as from about 5% to about 25%, such as from about 7.5% about 20%.

The molded parts discussed above may have a variety of different sizes and configurations. For instance, the molded parts may be used to form various parts used in "personal care" applications. For instance, in one particular embodiment, the molded part is used to form a tampon applicator that is water-dispersible.

Figure 2:
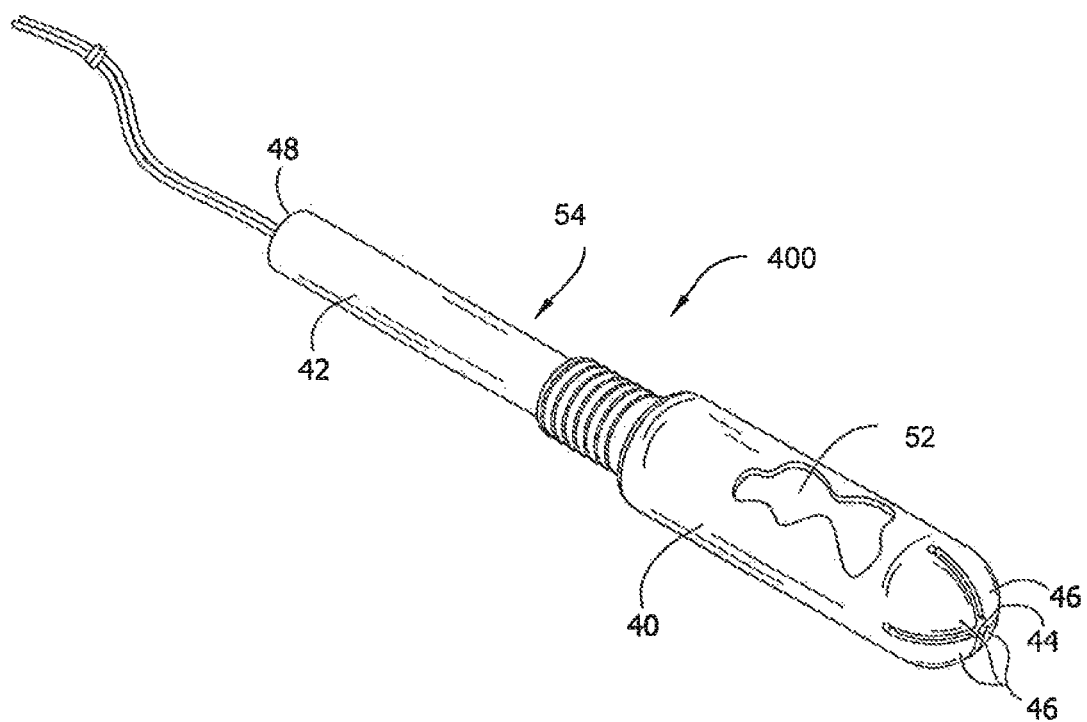
FIG. 2 is a perspective view of one embodiment of a water-dispersible tampon applicator as contemplated by the present invention.

As illustrated in the tampon assembly 400 of FIG. 2, the tampon applicator 54 comprises an outer tube 40 and an inner tube 42. The outer tube 40 is sized and shaped to house a tampon 52. A portion of the outer tube 40 is partially broken away in FIG. 2 to illustrate the tampon 52. In the illustrated embodiment, the outer tube 40 has a substantially smooth exterior surface, which facilitates insertion of the tampon applicator 54 without subjecting the internal tissues to abrasion. The outer tube 40 may be coated to give it a high slip characteristic. The illustrated outer tube 40 is a straight, elongated cylindrical tube. It is understood however that the applicator 54 could have different shapes and sizes than those illustrated and described herein.

Extending outwardly from the outer tube is an insertion tip 44. The insertion tip 44, which is formed as one-piece with the outer tube 40, may be dome-shaped to facilitate insertion of the outer tube into a woman's vagina in a comfortable manner. The illustrated insertion tip 44 is made of a thin, flexible material and has a plurality of soft, flexible petals 46 that are arranged to form the dome-shape. The petals 46 are capable of radially flexing (i.e., bending outward) to provide an enlarged opening through which the tampon 52 can exit when it is pushed forward by the inner tube 42. It is to be understood, however, that the outer tube 40 may be formed without the insertion tip 44. Without the insertion tip, the outer tube includes an opened end (not shown) through which the tampon 52 can exit when it is pushed forward by the inner tube.

The inner tube 42 is an elongate cylinder that is used to engage the tampon 52 contained in the outer tube 40. A free end 48 of the inner tube 42 is configured so that the user can move the inner tube with respect to the outer tube 40. In other words, the free end 48 functions as a grip for the forefinger of the user. The inner tube 42 is used to push the tampon 52 out of the outer tube 40 and into the woman's vagina by telescopically moving into the outer tube. As the inner tube 42 is pushed into the outer tube 40 by the user, the tampon 52 is forced forward against the insertion tip 44. The contact by the tampon 52 causes the petals 46 of the insertion tip 44 to radially open to a diameter sufficient to allow the tampon to exit the outer tube 40 and into the woman's vagina. With the tampon 52 properly positioned in the woman's vagina, the tampon applicator 54 is withdrawn. In a used configuration of the tampon applicator 54, the inner tube 42 is received in the outer tube 40.

The inner tube 42, the outer tube 40, and the insertion tip 44 can be formed from one or more layers, where one layer includes the water-dispersible, thermoplastic composition of the present invention. Further, to prevent the applicator 54 from prematurely disintegrating due to moisture during use and/or to reduce the coefficient of friction of the applicator 54 to make it more comfortable for the user, it can be coated with a water-insoluble material that also has a low coefficient of friction to enhance comfort and prevent disintegration during insertion of the applicator 54. Construction and operation of the tampon and tampon applicator described heretofore is conventional and known to those skilled in the art. The structure of the tampon applicator described above is conventional and known to those skilled in the art, and is described, for instance, in U.S. Pat. No. 8,317,765 to Loyd, et al., which is incorporated herein in its entirety by reference thereto for all purposes. Other tampon applicator structures that can be formed from the thermoplastic composition of the present invention are described, for instance, in U.S. Pat. No. 4,921,474 to Suzuki. et al. and U.S. Pat. No. 5,389,068 to Keck, as well as U.S. Patent Application Publication Nos. 2010/0016780 to VanDenBogart, et al. and 2012/0204410 to Matalish, et al., which are incorporated herein in their entirety by reference thereto for all purposes.

Figure 3:
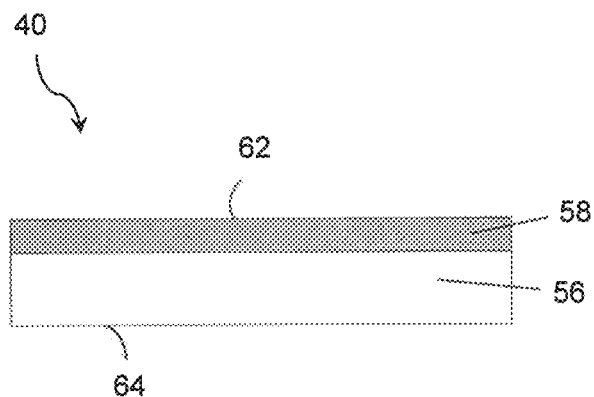
FIG. 3 is a cross-sectional view of one embodiment of a component of the tampon applicator of the present invention.

A cross-section of an outer tube 40 of tampon applicator 54, where the outer tube includes two layers, is shown in FIG. 3. The outer tube 40 can include an inner layer 56 having a tampon-facing surface 64 and an outer layer 58 having a body-facing surface 62. The inner layer 56 can be formed from the water-dispersible, thermoplastic composition of the present invention, while the outer layer 58 can be formed from a water-insoluble material that also has a low coefficient of friction to prevent the tampon applicator from becoming sticky upon use and introduction to a moist environment and to provide a smooth surface for insertion. For instance, the outer layer 58 can be a layer or coating of a wax, a silicon (e.g., polysiloxane), polytetrafluoroethylene, a polyolefin (e.g., polyethylene), a polyester, a polyamide, a thermoplastic elastomer (e.g., polyurethane or a polyolefin-based elastomer), or a combination thereof. It is also to be understood that while described above as a coating, the outer layer 58 can be an injection molded layer that can be formed prior to injecting the composition used to form the water-dispersible, inner layer 56.

The ratio of the weight percentage of the two layers can be selectively controlled to optimize the water-dispersibility of the tampon applicator, while at the same time not sacrificing the mechanical and physical properties required during use such that the applicator is stable when in contact with body fluids. Thus, the ratio of the weight percentage of the outer, body-facing layer to the weight percentage of the inner, tampon facing layer of the tampon applicator can be from about 0.005 to about 1, such as from about 0.0075 to about 0.75, such as from about 0.01 to about 0.5. For example, the applicator can comprise from about 1 wt. % to about 50 wt. % of the outer, water insoluble layer, such as from about 5 wt. % to about 40 wt. %, such as from about 10 wt. % to about 30 wt. %. On the other hand, the applicator can comprise from about 50 wt. % to about 99 wt. % of the inner, water-dispersible layer, such as from about 60 wt. % to about 95 wt. %, such as from about 70 wt. % to about 90 wt. %.

Figure 4:
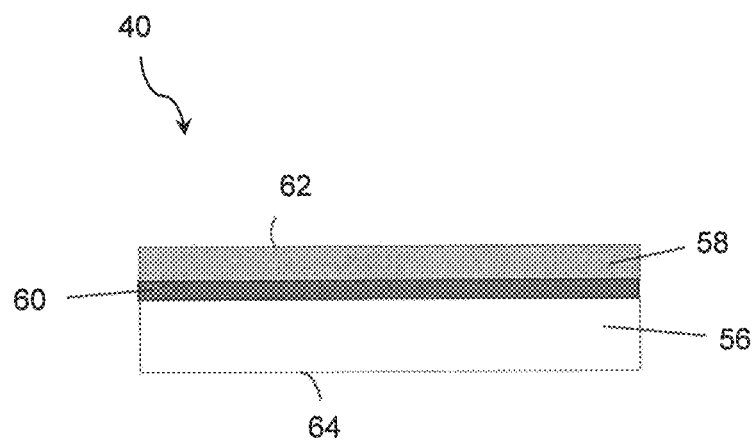
FIG. 4 is a cross-sectional view of another embodiment of a component of the tampon applicator of the present invention.

Meanwhile, FIG. 4 shows a cross section of an outer tube 40 of a tampon applicator 54, where the outer tube includes three layers. As in FIG. 3, the outer tube 40 can include an inner layer 56 having a tampon facing surface 64 and an outer layer 58 having a body facing surface 62. The inner layer 56 can be formed from the water-dispersible, thermoplastic composition of the present invention, while the outer layer 58 can be formed from a water-insoluble material to prevent the tampon applicator from becoming sticky upon use. For instance, the outer layer 58 can be a layer or coating of a wax, a silicon (e.g., polysiloxane), polytetrafluoroethylene, a polyolefin (e.g., polyethylene), a polyester, a polyamide, a thermoplastic elastomer (e.g., polyurethane or a polyolefin-based elastomer), any other suitable water-insoluble polymers, or a combination thereof. Further, a tie layer 60 between the inner layer 56 and the outer layer 58 can improve the adhesion between the inner layer 56 and the outer layer 58. This layer can be an adhesive material which bonds the outer layer 58 and the inner layer 56. Alternatively, the tie layer can be a block copolymer or a graft copolymer, for example, such copolymers may be the outer layer polymer grafted with a polar vinyl monomer (i.e., polyethylene grafted with maleic anhydride or hydroxyethyl methacrylate if the outer layer material is polyethylene, the graft copolymer has good adhesion with both of the layers.

Although FIGS. 3 and 4 only show cross-sections of an outer tube 40, it is to be understood that other components of the tampon applicator 54, such as the insertion tip 44 and/or the inner tube 42, particularly components that contact the body, can also be formed from the multilayered articles illustrated in FIGS. 3 and 4, to prevent the components from becoming sticky during use, which can be uncomfortable for the user.

The present invention may be better understood with reference to the following examples.

Test Methods

Melt Flow Rate

The melt flow rate ("MFR") is the weight of a polymer (in grams) forced through an extrusion rheometer orifice (0.0825-inch diameter) when subjected to a load of 2160 grams in 10 minutes, typically at 190° C. or 230° C. Unless otherwise indicated, melt flow rate is measured in accordance with ASTM Test Method D1239 with a Tinius Olsen Extrusion Plastometer.

Degree of Expansion

The degree of expansion of injection mold parts was determined by following ASTM D955-08 *Standard Test Method of Measuring Shrinkage from Mold Dimensions of Thermoplastics*. The injection mold cavity had a length ($L_m$) dimension of 126.78 mm and a width ($W_m$) dimension of 12.61 mm, which conforms to the ASTM D955-08 Type A specimen. The average length ($L_s$) and width ($W_s$) of specimens from Examples 1-4 were measured after 48±1 hour after the specimens had been removed from the mold. The shrinkage in the length direction ($S_l$) was calculated by $S_l=(L_m-L_s)\times 100/L_m$ and the shrinkage of the width direction ($S_w$) was calculated by $S_w=(W_m-W_s)\times 100/W_m$. Because negative shrinkage values represent expansion of the part, the degree of expansion in the width direction ("$E_l$") is equal to $-S_w$ and the degree of expansion in the length direction ("$E_l$") is equal to $-S_l$.

Tensile Properties

Tensile properties were determined by following ASTM D638-10 guidelines. ASTM D638-10 Type V injection molded test specimens were pulled via a MTS Mold 810 tensile frame with a 3,300 pound load cell. Five specimens were pulled from each example. The average values for peak stress (tensile strength), elongation at break, modulus, and elongation at yield were reported.

Overnight Still Water Disintegration Test

The disintegration of injection molded samples in tap water was tested by placing a small tensile bar sample having a weight of about 1 gram and in a container containing 200 milliliters of tap water. The samples were formed by injection molding in the manner described above. The samples were left overnight to observe dispersibility.

Slosh Box Water Disintegration Test

In the slosh box water disintegration test, rather than placing samples in still water that did not circulate, the samples were placed in 1500 milliliters of tap water pre-cooled to 15° C. Injection molded samples weighing between 4 grams and 5 grams and having a thickness of 0.05 inches were added to the pre-chilled water and rocked back and forth at a rate of 26 rotations per minute (rpm). The length of time until the samples were totally dispersed was recorded, with a target disintegration time of less than 180 minutes.

Example 1

A hydroxypropyl methylcellulose composition was formed as follows in an attempt to convert the hydroxypropyl methylcellulose into a melt extrudable, thermoplastic material. METHOCEL™ 40-100 hydroxypropyl methylcellulose was mixed together with glycerin prior to the extrusion process using a kitchen mixer. The hydroxypropyl methylcellulose (HPMC) and glycerin were mixed at 75:25 and 50:50 weight ratios of HPMC to glycerin. The resulting blends were then thermally processed using a 16 millimeter twin screw extruder immediately after mixing and after sitting overnight. The extrusion was conducted at varying temperatures. The various blends formed and their extrusion temperatures are shown below in Table 1.

The example was intended to convert METHOCEL™ 40-100 hydroxypropyl methylcellulose into a thermoplastic, melt extrudable material. At lower extrusion temperatures (100° C. to 140° C.), lighter colored powder resulted, and after extrusion, the compositions did not form coherent strands and therefore could not be considered thermoplastic. At extrusion temperatures of 140° C. to 160° C. and 160° C. to 180° C., some semi-converted strands were formed, but the HPMC was significantly degraded, as evidenced by the color of the strands darkening to brown or black. Further, because the polymer strands did not flow well and had many breaks, high extruder pressure resulted. No useful material could be produced from the attempted plasticization of the HPMC, and as a result, the materials extruded were not fully thermoplastic and not suitable for injection molding.

Further, materials that sat overnight did not process any better than the materials processed immediately after mixing the HPMC and glycerin. In addition, multiple screw speeds (100 rpm, 140 rpm, and 200 rpm) were attempted with no change in material appearance.

TABLE 1

METHOCEL ™ 40-100 Melt Processing Conditions

| Composition | Extrusion Temperature (° C.) | Observations from Extrudate |
|---|---|---|
| 75% HPMC/25% glycerin | 80-100 | Light tan powder |
| 75% HPMC/25% glycerin | 100-120 | Tan powder |
| 75% HPMC/25% glycerin | 120-140 | Brown powder |
| 75% HPMC/25% glycerin | 140-160 | Dark brown semi-converted powder |

TABLE 1-continued

METHOCEL ™ 40-100 Melt Processing Conditions

| Composition | Extrusion Temperature (° C.) | Observations from Extrudate |
|---|---|---|
| 75% HPMC/25% glycerin | 160-180 | Brown/black semi-converted powder |
| 50% HPMC/50% glycerin | 80-100 | Light tan powder |
| 50% HPMC/50% glycerin | 100-120 | Light tan powder |
| 50% HPMC/50% glycerin | 120-140 | Light tan powder |
| 50% HPMC/50% glycerin | 140-160 | Light brown semi-converted powder |
| 50% HPMC/50% glycerin | 160-180 | Brown semi-converted material |

Example 2

A hydroxypropyl methylcellulose composition was formed as follows in an attempt to convert the hydroxypropyl methylcellulose into a melt extrudable, thermoplastic material. METHOCEL™ 40-202 hydroxypropyl methylcellulose was mixed together with glycerin prior to the extrusion process using a kitchen mixer. The hydroxypropyl methylcellulose (HPMC) and glycerin were mixed at 75:25 weight ratios of HPMC to glycerin. The resulting blends were then thermally processed using a 16 millimeter twin screw extruder immediately after mixing and after sitting overnight. The extrusion was conducted at varying temperatures. The various blends formed and their extrusion temperatures are shown below in Table 2.

As observed in Example 1, the effort to convert HPMC into thermoplastic material failed, and when a one-hole die was used, the polymer strands did not flow well with many breaks in the strands and the extrudate, resulting in a high extruder pressure. Further, materials that sat overnight did not process any better than the materials processed immediately after mixing.

TABLE 2

METHOCEL ™ 40-202 Melt Processing Conditions

| Composition | Extrusion Temperature (° C.) | Observations from Extrudate |
|---|---|---|
| 75% HPMC/25% glycerin | 100-120 | White powder |
| 75% HPMC/25% glycerin | 120-140 | White powder |
| 75% HPMC/25% glycerin | 140-160 | White powder |
| 75% HPMC/25% glycerin | 160-180 | White powder |
| 75% HPMC/25% glycerin | 180-200 | Light brown semi-converted material |
| 75% HPMC/25% glycerin | 200-220 | Brown semi-converted material |

Example 3

A plasticized polyvinyl alcohol was formed as follows. ELVANOL™ 51-05 polyvinyl alcohol, a granular polymer having a degree of hydrolysis of 87.0-89.0 mole % and manufactured by DuPont, was compounded with glycerin and calcium carbonate at a 71:14:15 weight ratio utilizing a 43 mm twin screw extruder. A pelletizer (Conair, Bay City, Mich.) was used to cut the extruded strands to produce polyvinyl alcohol pellets. This plasticized PVOH is used in Examples 4-7 below.

Example 4

A plasticized blend of hydroxypropyl methylcellulose, polyvinyl alcohol, and calcium carbonate was formed as follows. Initially, METHOCEL™ 40-100 HPMC was mixed together with glycerin at a 50:50 weight ratio (125 grams of HPMC, 125 grams of glycerin). A Hobart kitchen aid mixer was used for mixing (model K5SS). 250 grams of the plasticized PVOH from Example 3 was then added to the pre-blended HPMC/glycerin at a 50:50 weight ratio. The blend was then thermally processed using a 16 mm twin screw extruder immediately after blending, where the extruder was heated to a temperature for zones 1 to 9 and the die of 170° C., 170° C., 170° C., 175° C., 175° C., 180° C., 185° C., 185° C., 190° C., and 190° C., respectively. The screw speed was set at 140 rpm to achieve a melt pressure of 9 bar and a torque of 20-22%. The extruded polymer was brown in color but flowed well. The strands were cooled and pelletized. The final composition is 35.5 wt. % PVOH, 25 wt. % HPMC, 32 wt. % glycerin, and 7.5 wt. % calcium carbonate based on the total weight of the polymer composition.

Example 5

A plasticized blend of hydroxypropyl methylcellulose, polyvinyl alcohol, calcium carbonate, and titanium dioxide was formed as follows. Initially, METHOCEL™ 40-100 HPMC was mixed together with glycerin at a 50:50 weight ratio (200 grams of HPMC, 200 grams of glycerin). A Hobart kitchen aid mixer was used for mixing (model K5SS). 375 grams of the plasticized PVOH from Example 3 and 38 grams of titanium dioxide white colorant were then added to the pre-blended HPMC/glycerin at a 50:50 weight ratio (e.g., 413 grams of the HPMC/glycerin blend was mixed with 413 grams of the plasticized PVOH/titanium oxide). The blend was then thermally processed using a 16 mm twin screw extruder immediately after blending, where the extruder was heated to a temperature for zones 1 to 9 and the die of 170° C., 170° C., 170° C., 175° C., 175° C., 180° C., 185° C., 185° C., 190° C., and 190° C., respectively. The screw speed was set at 140 rpm to achieve a melt pressure of 12 bar and a torque of 22-25%. The extruded polymer was white in color and flowed well from the die. The strands were cooled and pelletized. The final composition is 32.2 wt. % PVOH, 25 wt. % HPMC, 31.4 wt. % glycerin, 6.8 wt. % calcium carbonate, and 4.6 wt. % titanium dioxide based on the total weight of the polymer composition.

Example 6

A plasticized blend of hydroxypropyl methylcellulose, polyvinyl alcohol, calcium carbonate, and titanium dioxide was formed as follows. Initially, METHOCEL™ 40-100 HPMC was mixed together with glycerin at a 83:17 weight ratio (250 grams of HPMC, 50 grams of glycerin). A Hobart kitchen aid mixer was used for mixing (model K5SS). 250 grams of the plasticized PVOH from Example 3 and 55 grams of titanium dioxide white colorant were then added to the pre-blended HPMC/glycerin at a 50:50 weight ratio (e.g., 305 grams of the HPMC/glycerin blend was mixed with 305 grams of the plasticized PVOH/titanium oxide). The blend was then thermally processed using a 16 mm twin screw extruder immediately after blending, where the extruder was heated to a temperature for zones 1 to 9 and the die of 170° C., 170° C., 170° C., 175° C., 175° C., 180° C., 185° C., 185° C., 190° C., and 190° C., respectively. The screw speed was set at 140 rpm to achieve a melt pressure of 28 bar and a torque of 60-64%. The extruded polymer was white in color but did not flow well from the die. The strands were cooled and pelletized. This showed the effect of the level of glycerin on the flowability of the composition. The final composition is 29.1 wt. % PVOH, 41.7 wt. % HPMC, 14.1 wt. % glycerin, 6.1 wt. % calcium carbonate, and 9 wt. % titanium dioxide based on the total weight of the polymer composition.

Example 7

A plasticized blend of hydroxypropyl methylcellulose, polyvinyl alcohol, calcium carbonate, and titanium dioxide was formed as follows. Initially, METHOCEL™ 40-100 HPMC was mixed together with glycerin at a 63:37 weight ratio (250 grams of HPMC, 150 grams of glycerin). A Hobart kitchen aid mixer was used for mixing (model K5SS). 400 grams of the plasticized PVOH from Example 3 and 80 grams of titanium dioxide white colorant were then added to the pre-blended HPMC/glycerin at a 50:50 weight ratio (e.g., 480 grams of the HPMC/glycerin blend was mixed with 480 grams of the plasticized PVOH/titanium oxide). The blend was then thermally processed using a 16 mm twin screw extruder immediately after blending, where the extruder was heated to a temperature for zones 1 to 9 and the die of 170° C., 170° C., 170° C., 175° C., 175° C., 180° C., 185° C., 185° C., 190° C., and 190° C., respectively. The screw speed was set at 140 rpm to achieve a melt pressure of 18 bar and a torque of 30-35%. The extruded polymer was white in color and flowed well from the die. The strands were cooled and pelletized. The final composition is 29.6 wt. % PVOH, 31.3 wt. % HPMC, 24.6 wt. % glycerin, 6.2 wt. % calcium carbonate, and 8.3 wt. % titanium dioxide based on the total weight of the polymer composition.

The extrusion conditions for Examples 4-7 are set forth below in Table 3.

TABLE 3

Summary of Extrusion Conditions

| Sample | Extruder Speed (rpm) | $T_1$ | $T_2$ | $T_3$ | $T_4$ | $T_5$ | $T_6$ | $T_7$ | $T_8$ | $T_9$ | Die | Pressure (bar) | Torque (%) |
|---|---|---|---|---|---|---|---|---|---|---|---|---|---|
| Ex. 4 | 140 | 170 | 171 | 170 | 175 | 176 | 180 | 185 | 185 | 190 | 190 | 9 | 20-22 |
| Ex. 5 | 140 | 170 | 170 | 170 | 174 | 175 | 180 | 185 | 186 | 190 | 190 | 12 | 22-25 |
| Ex. 6 | 140 | 170 | 170 | 170 | 175 | 175 | 179 | 185 | 185 | 190 | 190 | 28 | 60-64 |
| Ex. 7 | 140 | 170 | 171 | 170 | 175 | 175 | 179 | 185 | 184 | 190 | 190 | 18 | 30-35 |

Example 8

Next, the water dispersibility of injection molded samples from examples 4-7 was determined based on the method described above. After sitting overnight, the samples had all dissolved into slurry and the tensile bars could not be identified.

Example 9

Samples from Examples 1-7 were tested for melt flow index and moisture content then processed for injection molding, where they were molded into tensile bars using a Boy Machine 22 ton injection molding press. The press had an ASTM test specimen mold with four (4) cavities. The temperature profile was 175° C., 178° C., 180° C. and 185° C. for zones 1 through 4. The mold was set at 50° F. and the cycle time was 69 seconds. Once formed, the specimens were tested for mold shrinkage (ASTM D955) and tensile properties (ASTM 0638). The results are provided below in Tables 4, 5, and 6.

To summarize, Examples 1 and 2 could not be thermally processed or injection molded. The mold would not fill fully for Example 3 due to the poor flowability of the composition. The resulting specimens were partially filled and yellow in color, and mold shrinkage and mechanical testing was not performed.

Meanwhile, the resulting specimens from Example 1 were brown in appearance and had a hard time ejecting from the mold due to stickiness. The specimens were flexible and not rigid. The resulting specimens from Example 2 were white in appearance and had a hard time ejecting from the mold. The specimens were very flexible, having almost a rubber feeling to them. The resulting specimens from Example 3 were dull white in color. The mold had a difficult time filling and could not be completely filled due to poor flowability and a low melt flow index of only 14 g/10 minutes. The specimens were very rigid and would break when bent. The materials of Examples 4, 5, and 7 could fill the mold completely, demonstrating good processability for injection molding. However, the resulting specimens from Example 4 were white in color and had a hard time ejecting from the mold. The specimens were very flexible, having almost a rubber feeling to them. Meanwhile, the material in Example 6 could not completely fill the mold due to the low melt flow rate, which can be attributed to the low level of plasticizer in Example 6.

TABLE 4

Melt Flow Index and Moisture Content

| Example | Melt Flow Index (g/10 minutes) | Moisture Content (ppm/%) |
|---|---|---|
| 1 | Could not be thermally processed | Could not be thermally processed |
| 2 | Could not be thermally processed | Could not be thermally processed |
| 3 | 14 | 12,000 (1.2%) |
| 4 | 60 | 17,000 (1.7%) |
| 5 | 70 | 14,000 (1.4%) |
| 6 | 0 | 8,300 (0.83%) |
| 7 | 23 | 11,700 (1.17%) |

TABLE 5

Degree of Expansion

| Example | $S_w$ | $E_w$ | $S_l$ | $E_l$ |
|---|---|---|---|---|
| 4 | −0.8% | +0.8% | +0.2% | −0.2% |
| 5 | −0.7% | +0.7% | +0.2% | −0.2% |
| 6 | −0.5% | +0.7% | +0.2% | −0.2% |
| 7 | −0.7% | +0.7% | +0.2% | −0.2% |

TABLE 6

Tensile Properties

| Example | Tensile Strength (MPa) | % Elongation at break | Modulus (MPa) | % Elongation at yield |
|---|---|---|---|---|
| 4 | 6 | 28% | 97 | 16% |
| 5 | 6 | 22% | 89 | 17% |
| 6 | 20 | 9% | 821 | 8% |
| 7 | 8 | 19% | 197 | 13% |

Example 10

In Example 10, various compositions including polyvinyl alcohol, hydroxypropyl methylcellulose, and other additives were extruded on a 30 mm twin screw extruder ZSK-30 to form thermoplastic homogeneous blends. The screw speed was 160 rpm and the temperature profile was 87° C., 129° C., 159° C., 190° C., 190° C., 184° C., and 145° C. for zones 1 through 7 of the extruder. The melt temperature was 170° C., the melt pressure was 50 pounds per square inch (psi), and the torque was 40%. The extruded materials were then molded into tensile bars using a Boy Machine 22 ton injection molding press. The press had an ASTM test specimen mold with four (4) cavities. The temperature profile was 185° C., 190° C., 195° C. and 200° C. for zones 1 through 4. The mold was set at 55° F. The examples were then tested for their mechanical properties and slosh box water disintegration times. Prior to molding the parts, the melt flow index of the compositions were also determined as discussed above.

TABLE 7

PVOH and HPMC Blends

| Example | PVOH (wt. %) | HPMC (wt. %) | Glycerin (wt. %) | Colorant (wt. %) | CaCO₃ Filler (wt. %) |
|---|---|---|---|---|---|
| 8 | 21 | 64 | 15 | — | — |
| 9 | 28 | 57 | 15 | — | — |
| 10 | 42 | 42 | 15 | — | — |
| 11 | 57 | 28 | 15 | — | — |
| 12 | 64 | 21 | 15 | — | — |
| 13 | 61 | 7 | 15 | 2 | 15 |
| 14 | 54 | 14 | 15 | 2 | 15 |
| 15 | 47 | 21 | 15 | 2 | 15 |

Examples 8-12 included CELVOL ™ 205 PVOH (5.2-6.2 cps viscosity, 87-89% hydrolysis)
Examples 13-15 included CELVOL ™ 502 PVOH (3.0-3.7 cps viscosity, 87-89% hydrolysis)
HPMC was METHOCEL ™ 40-100 PCG (18% Methoxyl, 5% hydroxypropyl, 12,000 cps viscosity)
Colorant was SCC 49487

TABLE 8

Properties of Examples 5-12

| Example | Melt Flow (grams/ 10 minutes) | Slosh Box Disintegration Time (minutes) | Tensile Strength (MPa) | % Elongation at break | Modulus (MPa) |
|---|---|---|---|---|---|
| 8 | — | — | — | — | — |
| 9 | — | — | — | — | — |
| 10 | <1 | >180 | 20 | 18 | 559 |
| 11 | 2 | 180 | 21 | 41 | 602 |
| 12 | 3 | 180 | 17 | 68 | 366 |
| 13 | 124 | 40 | 13 | 28 | 332 |
| 14 | 90 | 50 | 13 | 17 | 412 |
| 15 | 72 | 55 | 11 | 21 | 262 |

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A water-dispersible composition, the composition comprising:
   from about 7 wt. % to about 70 wt. % of at least one cellulose derivative, wherein the at least one cellulose derivative includes hydroxypropyl methylcellulose;
   from about 7 wt. % to about 70 wt. % of at least one synthetic water-soluble polymer; and
   from about 2 wt. % to about 50 wt. % of at least one plasticizer based on the total weight of the composition, wherein the weight percentage ratio of the synthetic water-soluble polymer to the cellulose derivative ranges from about 0.1 to about 10, further wherein the composition is thermoplastic.

2. The composition of claim 1, wherein the cellulose derivative constitutes from about 20 wt. % to about 60 wt. % of the composition based on the total weight of the composition.

3. The composition of claim 1, wherein the synthetic water-soluble polymer constitutes from about 20 wt. % to about 60 wt. % of the composition based on the total weight of the composition.

4. The composition of claim 1, wherein the plasticizer constitutes from about 5 wt. % to about 40 wt. % of the composition based on the total weight of the composition.

5. The composition of claim 1, wherein the weight percentage ratio of the synthetic water-soluble polymer to the cellulose derivative ranges from about 0.3 to about 3.

6. The composition of claim 1, wherein the hydroxypropyl methylcellulose has a methoxyl content of from about 10% to about 40%.

7. The composition of claim 1, wherein the hydroxypropyl methylcellulose has a hydroxypropyl content of from about 1% to about 15%.

8. The composition of claim 1, wherein the hydroxypropyl methylcellulose has a viscosity ranging from about 1,000 mPa·s to about 75,000 mPa·s for a 2% aqueous solution at 20° C.

9. The composition of claim 1, wherein the synthetic water-soluble polymer is a vinyl alcohol polymer.

10. The composition of claim 9, wherein the vinyl alcohol polymer is partially hydrolyzed.

11. The composition of claim 10, wherein the vinyl alcohol polymer has a degree of hydrolysis of from about 80 mole % to about 90 mole %.

12. The composition of claim 1, wherein the plasticizer is a polyhydric alcohol.

13. The composition of claim 12, wherein the plasticizer is a polyol.

14. The composition of claim 13, wherein the plasticizer is ethylene glycol, glycerol, propylene glycol, dipropylene glycol, butylene glycol, hexane triol, or a combination thereof.

15. The composition of claim 1, further comprising from about 0.5 wt. % to about 35 wt. % of an inorganic particulate filler based on the total weight of the composition.

16. The composition of claim 15, wherein the inorganic particulate filler comprises calcium carbonate, kaolin clay, silica, alumina, barium carbonate, sodium carbonate, titanium dioxide, zeolites, magnesium carbonate, calcium oxide, magnesium oxide, aluminum hydroxide, talc, or a combination thereof.

17. The composition of claim 1, wherein the composition exhibits a melt flow index of from about 10 grams per 10 minutes to about 150 grams per 10 minutes when subjected to a load of 2160 grams at a temperature of 190° C. according to ASTM Test Method D1238-E.

18. The composition of claim 1, wherein the composition is injection moldable.

19. A molded article comprising the composition of claim 1.

20. The molded article of claim 19, wherein the molded article disintegrates in still tap water in less than about 18 hours.

21. The molded article of claim 19, wherein the molded article is a tampon applicator.

22. A method for forming an injection molded part, the method comprising:

injecting a water-dispersible, thermoplastic composition into a mold cavity, wherein the thermoplastic composition comprises from about 7 wt. % to about 70 wt. % of a cellulose derivative, from about 7 wt. % to about 70 wt. % of a synthetic water-soluble polymer, wherein the synthetic water-soluble polymer comprises polyvinyl alcohol, and from about 2 wt. % to about 50 wt. % of a plasticizer; and shaping the thermoplastic composition into a molded part within the mold cavity.

23. The method of claim 22, further comprising coating the injection molded part with a water-insoluble coating.

24. The method of claim 22, further comprising a co-injection molding process, wherein the injection molded part is a two layered molded part having an inner layer and an outer layer, wherein the inner layer comprises the injection-molded, thermoplastic composition and the outer layer is water-insoluble.

25. The method of claim 24, wherein the outer layer comprises from about 1 wt. % to about 50 wt. % of the injection molded part and the inner layer comprises from about 50 wt. % to about 99 wt. % of the injection molded part.

26. The method of claim 24, wherein the outer layer comprises a wax, silicon, polytetrafluoroethylene, polyethylene, a polyester, polyamide, a thermoplastic elastomer, or a combination thereof.

27. The method of claim 22, wherein the cellulose derivative comprises hydroxypropyl methylcellulose.

28. The method of claim 22, wherein the molded part is a tampon applicator.

* * * * *